United States Patent
Zeevi

(10) Patent No.: US 11,707,303 B2
(45) Date of Patent: Jul. 25, 2023

(54) MULTI-LEVEL VERTEBRAL IMPLANT SYSTEM

(71) Applicant: Premia Spine Ltd., Ramat Poleg (IL)

(72) Inventor: Tal Zeevi, Karkur (IL)

(73) Assignee: Premia Spine Ltd., Ramat Poleg (IL)

( * ) Notice: Subject to any disclaimer, the term of this patent is extended or adjusted under 35 U.S.C. 154(b) by 13 days.

(21) Appl. No.: 16/626,448

(22) PCT Filed: Jun. 19, 2018

(86) PCT No.: PCT/IB2018/054490
§ 371 (c)(1),
(2) Date: Dec. 24, 2019

(87) PCT Pub. No.: WO2019/003048
PCT Pub. Date: Jan. 3, 2019

(65) Prior Publication Data
US 2020/0129210 A1    Apr. 30, 2020

Related U.S. Application Data

(60) Provisional application No. 62/524,549, filed on Jun. 25, 2017.

(51) Int. Cl.
*A61B 17/70* (2006.01)
*A61B 17/00* (2006.01)

(52) U.S. Cl.
CPC ...... *A61B 17/7049* (2013.01); *A61B 17/7043* (2013.01); *A61B 2017/00991* (2013.01)

(58) Field of Classification Search
CPC .............. A61B 17/7043; A61B 17/7049–7052
See application file for complete search history.

(56) References Cited

U.S. PATENT DOCUMENTS

| | | | | |
|---|---|---|---|---|
| 5,147,359 A | * | 9/1992 | Cozad | A61B 17/7008 606/276 |
| 5,387,212 A | * | 2/1995 | Yuan | A61B 17/701 606/264 |
| 5,437,669 A | * | 8/1995 | Yuan | A61B 17/704 606/264 |

(Continued)

FOREIGN PATENT DOCUMENTS

| | | |
|---|---|---|
| EP | 1693012 | 8/2006 |
| FR | 2781359 | 1/2000 |

OTHER PUBLICATIONS

PCT Search Report and Written Opinion PCT/IB2018/054490, dated Oct. 30, 2018.

*Primary Examiner* — Eduardo C Robert
*Assistant Examiner* — Steven J Cotroneo
(74) *Attorney, Agent, or Firm* — Dekel Patent Ltd.; David Klein

(57) ABSTRACT

A spinal implant system (10) includes a superior attachment rod (12) coupled to, and articulating with respect to, a roller housing (17), an inferior cross bar member (20) coupled to the roller housing (17), and an inferior attachment rod (14) coupled to the inferior cross bar member (20). At least one of the superior and inferior attachment rods (12, 14) is supported by a flexure assembly (16). The inferior attachment rod (14) is coupled to the inferior cross bar member (20) with a swivel joint (32) and/or a telescoping portion (20).

9 Claims, 4 Drawing Sheets

(56) References Cited

U.S. PATENT DOCUMENTS

| | | | |
|---|---|---|---|
| 5,486,174 A * | 1/1996 | Fournet-Fayard | ............................ A61B 17/7037 403/122 |
| 5,702,392 A * | 12/1997 | Wu | ..................... A61B 17/7008 606/250 |
| 6,916,319 B2 * | 7/2005 | Munting | ............ A61B 17/7043 606/250 |
| 7,220,262 B1 | 5/2007 | Hynes | |
| 7,604,652 B2 * | 10/2009 | Amin | ................. A61B 17/7043 606/249 |
| 9,687,277 B2 * | 6/2017 | Wessels | .............. A61B 17/7031 |
| 10,010,426 B2 * | 7/2018 | Kuiper | ................... A61F 2/4405 |
| 10,842,539 B2 * | 11/2020 | Faulhaber | ................ A61F 2/447 |
| 2006/0200130 A1 * | 9/2006 | Hawkins | ............ A61B 17/7043 606/86 A |
| 2007/0093833 A1 * | 4/2007 | Kuiper | ................... A61F 2/4405 606/86 A |
| 2008/0243186 A1 * | 10/2008 | Abdou | ................ A61B 17/7032 606/246 |
| 2012/0109202 A1 | 5/2012 | Kretzer | |
| 2014/0074166 A1 * | 3/2014 | Scarrow | .............. A61B 17/7064 606/247 |
| 2014/0188176 A1 * | 7/2014 | Iott | ........................ A61B 17/70 606/279 |

\* cited by examiner

MULTI-LEVEL VERTEBRAL IMPLANT SYSTEM

FIELD OF THE INVENTION

The present invention relates generally to spinal implants, and particularly to spinal implants for attachment at adjacent levels in the lumbar spine or between the lumbar and sacral vertebral levels.

BACKGROUND OF THE INVENTION

The present invention relates generally to spinal fixation devices for the internal fixation of the spine particularly within the fields of orthopedics and/or neurosurgery such as spinal implants and rods for holding vertebral bones fixed relative to one another and, more particularly, to a polyaxial pedicle screw and/or coupling apparatus for use in spinal surgical procedures for receiving a rod for stabilizing the relative motion of vertebrae.

Spinal stenosis, as well as spondylosis, spondylolisthesis, osteoarthritis and other degenerative phenomena may cause back pain, especially lower back pain. Such phenomena may be caused by a narrowing of the spinal canal by a variety of causes that result in the pinching of the spinal cord and/or nerves in the spine. Fusion of two or more adjacent vertebrae has been used to alleviate back pain. However, fusion of vertebrae can be disfavored because fusion tends to cause degenerative phenomena in the fused vertebrae to migrate to adjacent vertebral components that have not been fused.

In contradistinction to spinal fusion, U.S. Pat. Nos. 7,011,685 and 7,811,308 (and others) describe a total posterior spine implant system that allows axial rotation, lateral bending, extension, and flexion. The implant facilitates bending, straightening and twisting movements at the affected segment of the spine while blocking excessive posterior and anterior sagittal translation. The system stabilizes, but does not fuse, the affected vertebral level following decompression surgery to alleviate pain stemming from degenerative spondylolisthesis, spinal stenosis or other conditions.

Further spinal implant systems address multi-level diseases of the spine, such as patients suffering from lumbar spinal disease at one or two adjacent levels between L1 and S1 that would otherwise entail decompression and stabilization by fixation.

SUMMARY OF THE INVENTION

The present invention seeks to provide spinal implants for attachment at adjacent levels in the lumbar spine or between the lumbar and sacral vertebral levels, as is described more in detail hereinbelow.

One of the advantages of the invention over the prior art is that the structure of the spaced-apart inferior attachment rods (which extend from a cross bar member) enables minimal bone and tissue removal, because this U-shaped or C-shaped cross bar structure extends down to a lower level or up to an upper level of the spine without increasing the size of the implant body.

In one non-limiting embodiment, the spinal implant system includes a superior attachment rod coupled to, and articulating with respect to, a roller housing, an inferior cross bar member coupled to the roller housing, an inferior attachment rod coupled to the inferior cross bar member, wherein at least one of the superior and inferior attachment rods is supported by a flexure assembly, and wherein the inferior attachment rod is coupled to the inferior cross bar member with at least one of a swivel joint and a telescoping portion.

In one non-limiting embodiment, the flexure assembly includes an elastomeric cushion.

In one non-limiting embodiment, the superior attachment rod passes through an aperture formed in the roller housing, the aperture being larger than the flexure assembly so as to increase degrees of freedom of movement in which the superior attachment rod can move.

In one non-limiting embodiment, there is more than one inferior attachment rod and they are movable independently of each other.

In one non-limiting embodiment, there is more than one inferior attachment rod and they are coupled to a common swivel joint and are movable together symmetrically with respect to each other.

In one non-limiting embodiment, the telescoping portion slides in the inferior cross bar member.

In one non-limiting embodiment, the swivel joint includes a ball-and-socket joint.

BRIEF DESCRIPTION OF THE DRAWINGS

The present invention will be understood and appreciated more fully from the following detailed description, taken in conjunction with the drawings in which.

DETAILED DESCRIPTION OF EMBODIMENTS

Figure 1A:
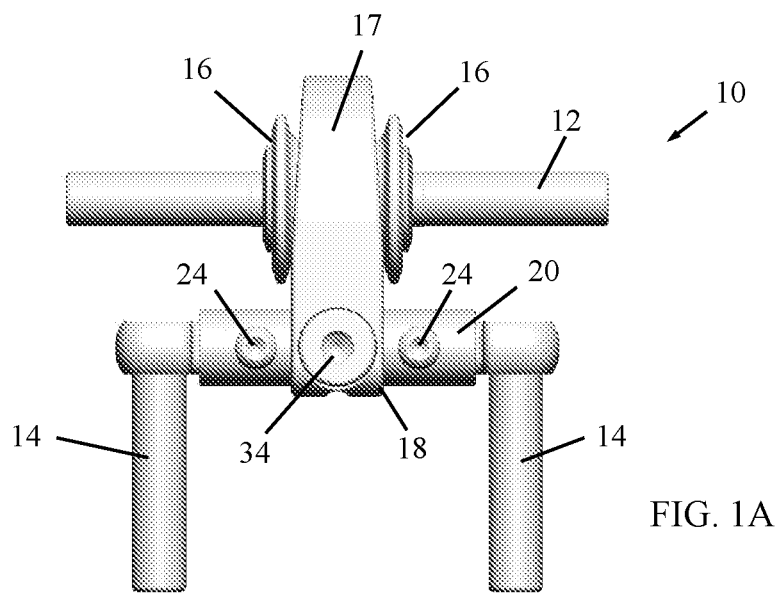
FIGS. 1A and 1B are simplified front view and pictorial illustrations, respectively, of a spinal implant system, constructed and operative in accordance with a non-limiting embodiment of the present invention, having superior attachment rods supported by a flexure assembly and inferior attachment rods, which may be telescoping and which may rotate about a rotation axis.
Figure 1B:
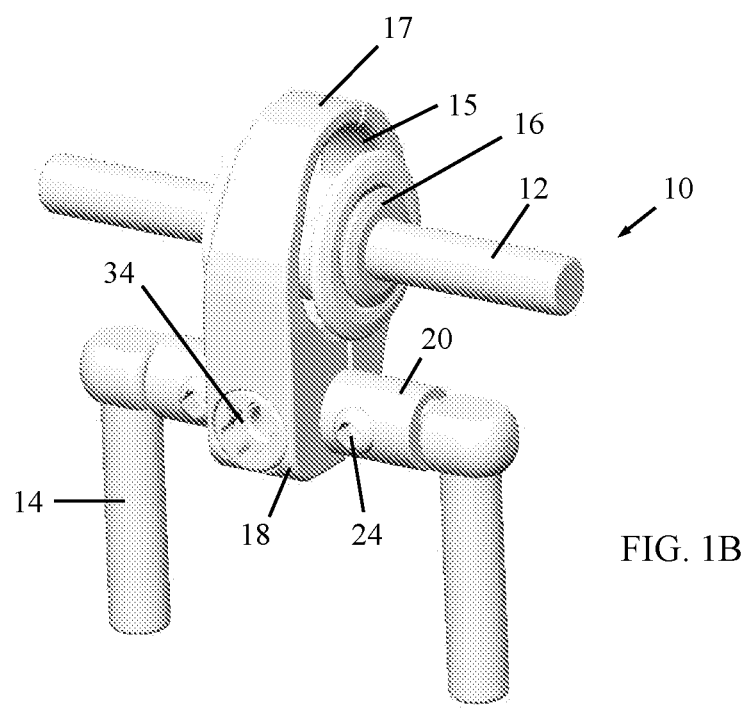

Reference is now made to FIGS. 1A and 1B, which illustrate a spinal implant system 10, constructed and operative in accordance with a non-limiting embodiment of the present invention.

System 10 includes one or more superior attachment rods 12 and one or more inferior attachment rods 14. The term "rod" encompasses any projecting member of any shape, cross-sectional shape and size, such as but not limited to, rod, bar, prong, beam, lug and the like. The terms "superior" and "inferior" refer to the illustrations, but it is understood that when installed, the superior attachment rod can be attached to vertebral structure that is either superior or inferior to the inferior attachment rod.

The superior attachment rod or rods 12 may be supported by a flexure assembly 16, such as an elastomeric cushion in which one portion of the rod is supported or held as in a bearing. Due to the flexibility of the elastomeric cushion, the rod 12 is free to move (e.g., translate, tilt or rotate) in any direction and the elastomeric cushion limits the amount of movement. In the illustrated embodiment, there is one rod 12 that passes through two flexure assemblies 16 and through an aperture 15 formed in a roller housing 17. As seen in FIG. 1B, aperture 15 is larger than the flexure assemblies 16 so as to increase the degrees of freedom of movement in which the rod 12 can move.

It is noted that although one superior attachment rod 12 is used in the illustrated embodiment, and the description will follow for this structure, nevertheless for certain applications more than one rod may be used. For example, instead of one rod passing through housing 17, two individual rods may be used, each of which has a lateral end supported in one of the flexure assemblies 16. It is also noted that although two inferior attachment rods 14 are used in the illustrated embodiment, nevertheless for certain applications one rod 14 or more than two rods 14 may be used.

Figure 2A:
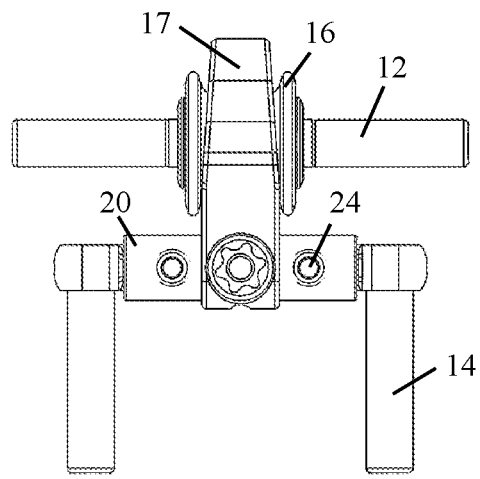
FIGS. 2A and 2B are simplified front view illustrations, respectively, before and after moving the inferior attachment rods laterally.
Figure 2B:
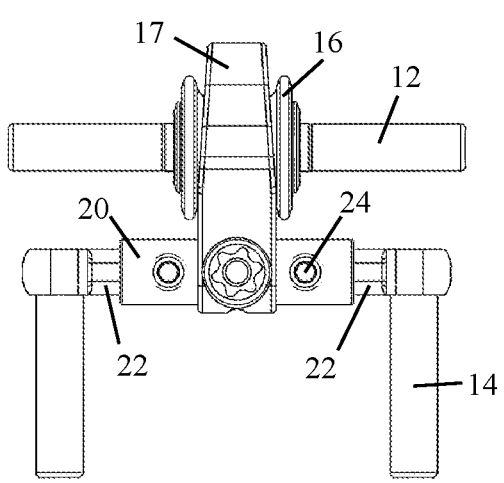

An inferior portion 18 of housing 17 houses an inferior cross bar member 20 from which extend the inferior attachment rods 14. As seen in FIGS. 2A and 2B, the inferior attachment rods 14 may extend from a telescoping portion 22 (seen in FIG. 2B) that slides in inferior cross bar member 20. Lateral and medial (or other side-to-side) movement of telescoping portion 22 is used to determine the lateral or medial (or other side-to-side) position of each inferior attachment rod 14. Additionally, inferior attachment rods 14 may rotate about a rotation axis, such as the longitudinal axis of telescoping portion 22. A fastener 24, such as a set screw, may be used to fix the position and orientation of the rods 14.

Figure 3:
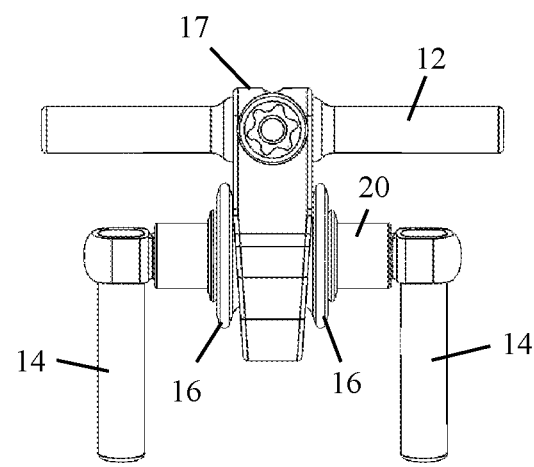
FIG. 3 is a simplified front view illustration of another version of the spinal implant system of FIGS. 1A and 1B, in which the inferior attachment rods are supported by a flexure assembly.

Reference is now made to FIG. 3, which illustrates another version of the spinal implant system of FIGS. 1A and 1B, in which the inferior attachment rods are supported by flexure assemblies 16. Alternatively, both superior and inferior rods may be supported by flexure assemblies.

Figure 4A:
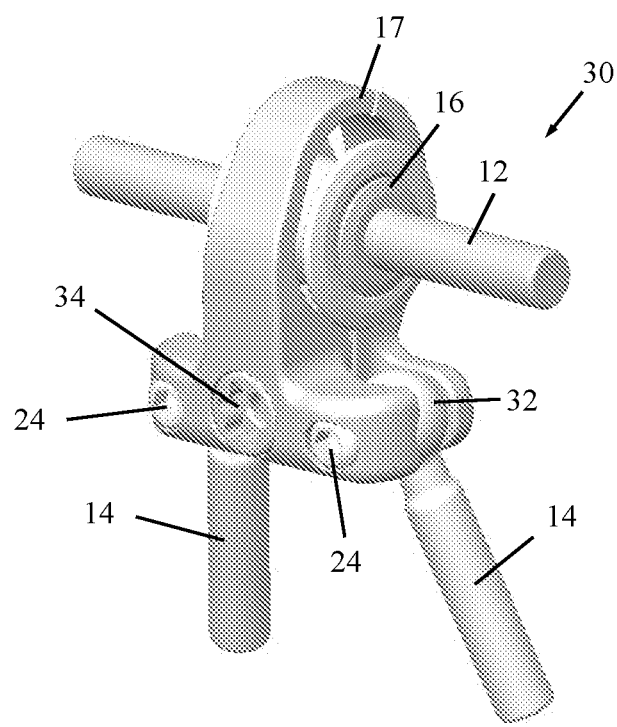
FIGS. 4A and 4B are simplified pictorial and front view illustrations, respectively, of a spinal implant system, constructed and operative in accordance with another non-limiting embodiment of the present invention, having superior attachment rods supported by a flexure assembly and inferior attachment rods coupled directly to the roller housing with a ball-and-socket joint, which may swivel or rotate about multiple axes, wherein in FIG. 4B the inferior attachment rods move independently of each other.
Figure 4B:
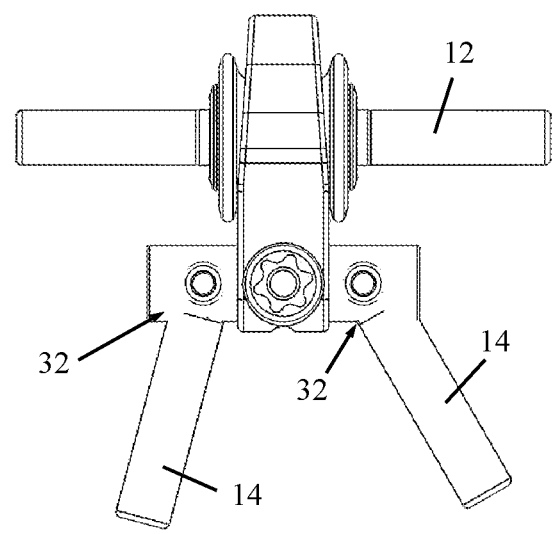

Reference is now made to FIGS. 4A and 4B, which illustrate a spinal implant system 30, constructed and operative in accordance with another non-limiting embodiment of the present invention. Spinal implant system 30 is similar to spinal implant system 10, with like elements being designated by like reference numerals.

Spinal implant system 30 differs from spinal implant system 10 in that inferior attachment rods 14 are not telescoping, but instead are connected to the inferior portion 18 of housing or to the inferior cross bar member 20 with a swivel joint 32, such as a ball-and-socket joint. In this manner, inferior attachment rods 14 may articulate with respect to the rest of the implant in multiple degrees of freedom or multiple axes of rotation.

Figure 4C:
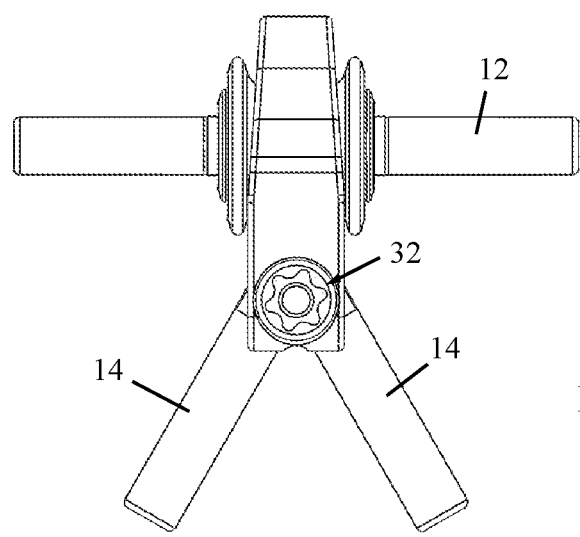
FIG. 4C is a simplified front view illustration of another version of the spinal implant system of FIG. 4B, in which the inferior attachment rods move together symmetrically with respect to each other.

In FIG. 4B, the inferior attachment rods 14 can move independently of each other. In contrast, in the embodiment of FIG. 4C, the inferior attachment rods 14 are connected to a common swivel joint 32 and can move together symmetrically with respect to each other.

Figure 5A:
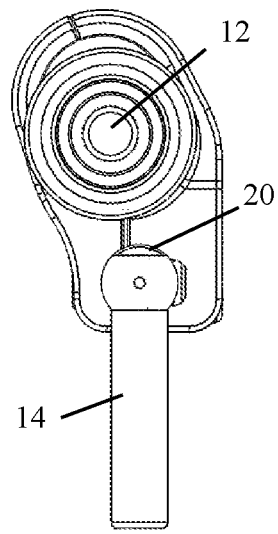
FIGS. 5A, 5B and 5C are simplified front view illustrations of different angular orientations of the inferior attachment rods of any of the embodiments of the invention.
Figure 5B:
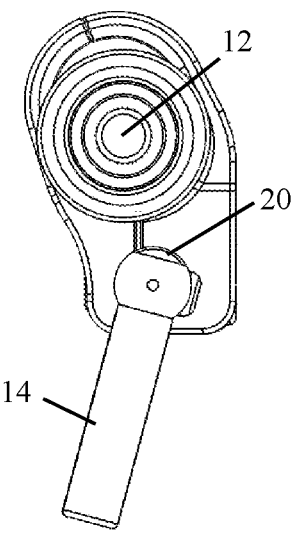
Figure 5C:
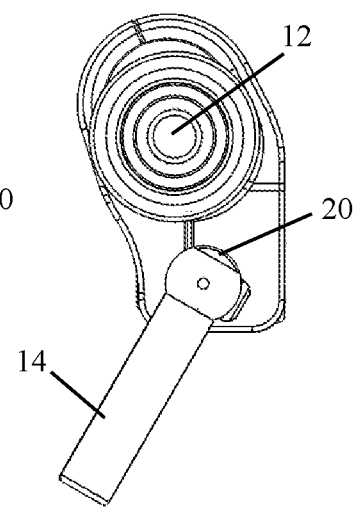

FIGS. 5A, 5B and 5C illustrate different angular orientations of the inferior attachment rods 14 of any of the embodiments of the invention. The inferior attachment rod 14 may be coupled to inferior cross bar member 20 with both a swivel joint and a telescoping portion.

Non-limiting materials which may be used to construct any of the embodiments of the invention include CoCrMo low carbon ASTM 1537 UNS R3 1537; Ti-6Al-4V ELI per ASTM F136; Ti-6Al-4V ELI PER ASTM F-2885. The articulating surfaces of the roller housing 17 and of the rods 12 or 14 may be made of coated materials, such as but not limited to: crosslinked UHMWPE (ultra-high molecular weight polyethylene), blended with Vitamin E, per ISO 5834 part 1; crosslinked UHMWPE, per ISO 5834 part 1; CoCrMo low carbon ASTM 1537 UNS R3 1537; Ti-6Al-4V ELI per ASTM F136, ceramic coated; Ti-6Al-4V ELI PER ASTM F-2885, ceramic coated.

Figure 6A:
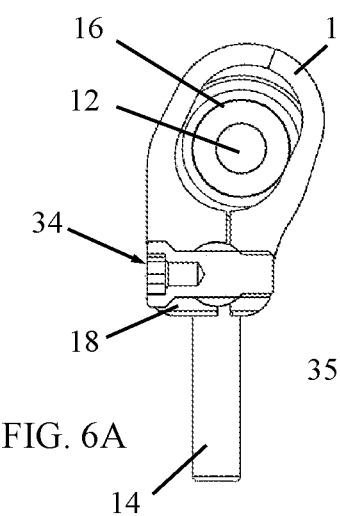
FIGS. 6A and 6B are simplified pictorial and enlarged illustrations, respectively, of a locking fastener used in any of the embodiments of the invention.
Figure 6B:
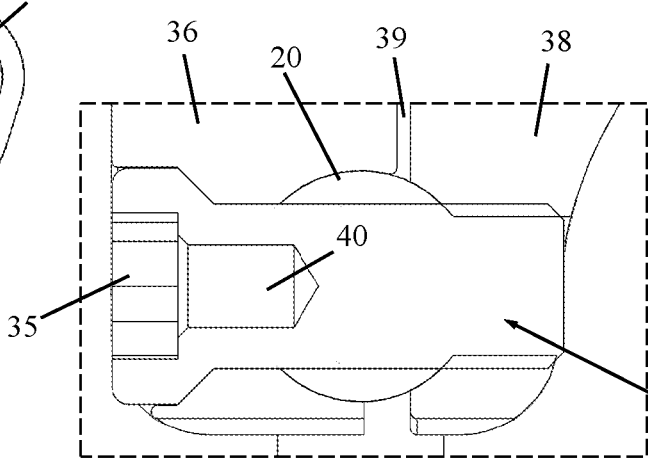

Reference is now made to FIGS. 6A and 6B, which illustrate a locking fastener 34, which can be used in any of the embodiments of the invention.

Locking fastener 34 may be a threaded fastener with any suitable fastener head 35, such as but not limited to, TORX (hexalobular) or Philips or others. As seen best in FIG. 6B, locking fastener 34 passes through a posterior portion 36 of the inferior portion 18 of housing 17 (the numerals 17 and 18 being shown in FIG. 6A), through inferior cross bar member 20 and then into an anterior portion 38 of the inferior portion 18 of housing 17. The fastener head 35 thus faces outwards in the posterior direction. A gap 39 may be formed between posterior portion 36 and anterior portion 38 of the inferior portion 18 of housing 17. By tightening locking fastener 34, the posterior portion 36 and anterior portion 38 are tightened together (gap 39 diminishes in size) and this locks inferior cross bar member 20 in place. The posterior portion 36 and anterior portion 38 are tightened around inferior cross bar member 20.

Locking fastener 34 may be formed with an inner threaded bore 40, to which one can attach an instrument, such as for inserting the implant.

What is claimed is:

1. A spinal implant system comprising:
  a superior attachment rod coupled to, and articulating with respect to, a roller housing, wherein said superior attachment rod passes through a hole formed in said roller housing, said hole being larger than an outer diameter of said superior attachment rod such that said superior attachment rod can tilt and radially translate with respect to said hole;
  an inferior cross bar member coupled to said roller housing;
  an inferior attachment rod coupled to said inferior cross bar member, wherein a flexure assembly is mounted on said superior attachment rod and said hole is larger than an outer diameter of said flexure assembly such that there is a gap between the inner diameter of said hole and the outer diameter of said flexure assembly so that said superior attachment rod and said flexure assembly are not clamped in said hole but instead tilt and radially translate with respect to said hole; and
  wherein said inferior attachment rod comprises at least two inferior attachment rods which are coupled to said inferior cross bar member with a common swivel joint and a telescoping portion, wherein side-to-side movement of said telescoping portion determines a side-to-side position of said inferior attachment rods, and wherein said inferior attachment rods are rotatable about a longitudinal axis of said telescoping portion.

2. The spinal implant system according to claim 1, wherein said flexure assembly comprises an elastomeric cushion.

3. The spinal implant system according to claim 1, wherein said inferior attachment rods are movable independently of each other.

4. The spinal implant system according to claim 1, wherein said inferior attachment rods are movable together symmetrically with respect to each other.

5. The spinal implant system according to claim 1, wherein said telescoping portion slides in said inferior cross bar member.

6. The spinal implant system according to claim 1, wherein said swivel joint comprises a ball-and-socket joint.

7. The spinal implant system according to claim 1, wherein said superior attachment rod is free to translate, tilt or rotate in any direction, including rotating about a longitudinal axis of said superior attachment rod.

8. The spinal implant system according to claim 1, wherein said inferior attachment rods articulate with respect to the implant system in multiple axes of rotation.

9. The spinal implant system according to claim 1, wherein a fastener is used to fix the side-to-side position of said inferior attachment rods and a rotational orientation of said inferior attachment rods about the longitudinal axis of said telescoping portion.

\* \* \* \* \*